Figure 1:
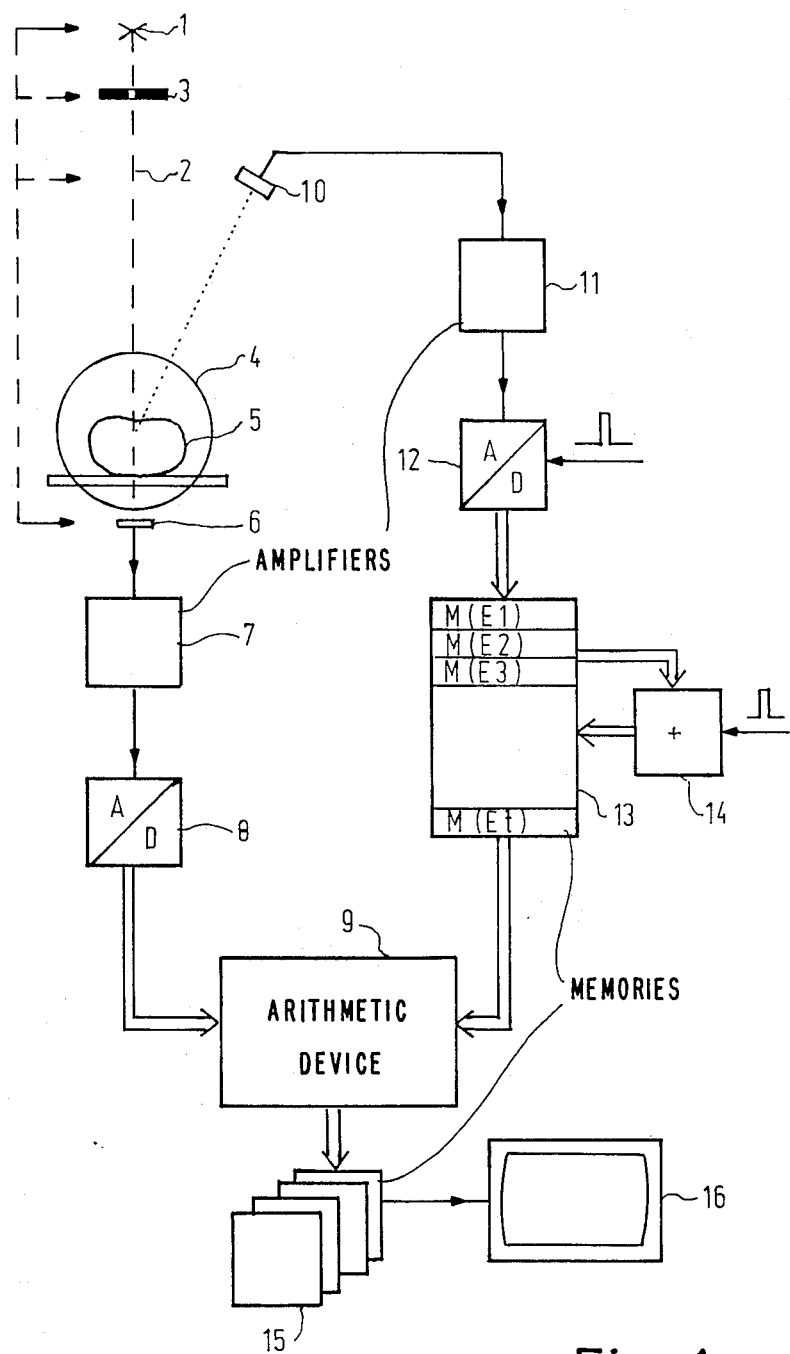

United States Patent [19]
Harding et al.

[11] Patent Number: 4,850,002
[45] Date of Patent: Jul. 18, 1989

[54] TWO-DIMENSIONAL COMPTON PROFILE IMAGING METHOD

[75] Inventors: Geoffrey Harding, Halstenbek; Josef-Maria Kosanetzky, Norderstedt; Ulrich Neitzel, Hamburg, all of Fed. Rep. of Germany

[73] Assignee: U.S. Philips Corporation, New York, N.Y.

[21] Appl. No.: 92,805

[22] Filed: Sep. 3, 1987

[30] Foreign Application Priority Data

Sep. 9, 1986 [DE] Fed. Rep. of Germany ....... 3630651

[51] Int. Cl.$^4$ .......................................... G01N 23/203
[52] U.S. Cl. ........................................ 378/87; 378/90; 378/6
[58] Field of Search .................... 378/6, 62, 86, 87, 90

[56] References Cited

U.S. PATENT DOCUMENTS 4,375,695 3/1983 Harding et al. .......................... 378/6
4,384,209 5/1983 Wagner et al. .......................... 378/6

OTHER PUBLICATIONS

R. S. Holt et al., Assessment of Gamma Ray Scattering for the Characterisation of Biological Material, Phys. Med. Biol., 1983, vol. 28, No. 12, pp. 1435–1440.
Samim Anghaie et al., Atomic Composition Measurement in Vivo Using Compton Profile Methods, Trans. Am. Mucl. Soc. 47, 1984, pp. 38–39.
Trans Am. Mucl. Soc. 47, 1984 pp. 39-40
Atomic Composition Measurement in Vivo using Compton . . .
Phys. Med. Biol. 1983 No. 12 1435-1440.
Assessment of Gamma Ray Scattering . . .

Primary Examiner—Carolyn E. Fields
Assistant Examiner—David P. Porta
Attorney, Agent, or Firm—Jack E. Haken

[57] ABSTRACT

The invention relates to a method of determining the Compton profile of an object to be examined which is situated in an examination zone. The examination zone is irradiated by a monochromatic primary beam whose energy is chosen so that the attenuation of the primary radiation is due essentially only to the Compton Scattering. The scattered radiation is measured in an energy resolving manner and therefrom, as well as from the attenuation in the primary beam, the Compton profiles for the individual pixels in the examination zone are determined.

9 Claims, 3 Drawing Sheets

TWO-DIMENSIONAL COMPTON PROFILE IMAGING METHOD

The invention relates to a two-dimensional Compton profile imaging method, i.e. a method in which the Compton profile for an examination zone can be determined as a function of location, as well as to a device for performing the method.

It is known that Compton scattered radiation has a wavelength which exceeds that of the initiating primary gamma rays or X-rays and that for a predetermined wavelength of the primary radiation and a predetermined angle of scattering the intensity of the scattered radiation exhibits a maximum at a defined wavelength. However, on both sides of this wavelength the intensity of the radiation scattered within the relevant angle is not zero, so that a wider intensity spectrum arises. This spectrum, or the intensity of the Compton scattered radiation as a function of the pulse transfer (which is unambiguously determined by the wavelength and the scatter angle), is referred to as a Compton profile.

Recent studies have revealed that the Compton profile of a biological tissue depends on the constitution thereof (Phys. Med. Biol., Vol. 28, p.1435, 1984). The same is applicable to semiconductor materials.

Therefore, it is an object of the present invention to provide a two-dimensional Compton profile imaging method, that is to say a method which enables determination of the Compton profile in the individual pixels of a layer.

This object is achieved in accordance with the invention in that an examination zone is irradiated by means of a monochromatic primary beam which has a small crosssection and whose energy is chosen so that the attenuation of the primary beam is caused essentially by Compton scattering, the intensity of the primary beam after its passage through the examination zone being measured by means of a first detector, a second detector measuring, in dependence of the wavelength, the intensity of the scattered radiation emerging at a predetermined angle with respect to the primary beam, the measurement being repeated for a multitude of parallel beam paths which extend through the examination zone in a multitude of directions, the attenuation of the primary beam in the individual pixels being reconstructed from the measurement values of the first detector, the Compton scatter density in dependence of the quantum energy in the pixels of the examination zone being given and therefrom, taking into account their attenuation, the intensity of the Compton scattered-radiation at the location of the second detector is calculated for each beam path, from the difference between the calculated intensity and the measured intensity for the relevant beam path there being formed a correction value for correcting the given Compton scatter density in the individual pixels.

The imaging method in accordance with the invention is based on the fact that first the scatter density relating to the scatter angle is given as a function of the energy for each pixel. On the basis thereof, for each pixel situated along the beam path followed by the primary beam during the measurement the intensity of the scattered radiation at the location of the second detector can be determined as a function of the energy of the scattered radiation when the intensity of the primary radiation is known and when the attenuation incurred by the radiation on its way to the relevant pixel (as primary radiation) and further to the detector (as scattered radiation) is also known. The sum of the scatter intensities supplied by all pixels along a beam path should correspond to the measured intensity when the given Compton profile corresponds to the actual circumstances. Generally this is not the case; however, from the difference between the calculated and the measured value of the scatter intensity there can be derived a correction value which is distributed between the individual pixels along the beam path. After this correction, the Compton profile thus calculated for the individual pixels already corresponds better to reality; this approximation can be further improved by further iteration steps.

In order to determine the Compton profile, use must be made of a suitable monochromatic radiation source whose radiation has such an energy or wavelength that the radiation is attenuated essentially only by Compton scattering. It is only in that case that the attenuation of the scattered radiation, having a lower energy or a longer wavelength, can be calculated from the transmission tomogram formed by means of the signals of the first detector.

A device for performing this method is characterized in that it comprises a radiation source for generating monochromatic radiation, a primary beam diaphragm for forming a primary beam which passes through the examination zone and which has a small cross-section, a first detector which is arranged in the primary beam, an energy-resolving second detector which intercepts the scattered radiation emerging at a defined angle, a pulse amplitude analyzer which is coupled thereto, and an arithmetic device which is coupled to the pulse amplitude analyzer and which iteratively determines the Compton profile in the pixels of the examination zone from the measurement values of the detectors.

A preferred embodiment in accordance with the invention is characterized in that the angle enclosed by the scattered radiation detected by the second detector with respect to the primary beam is larger than 90°. The invention can in principle be used for an arbitrary scatter angle, by particularly favourable circumstances arise when the backscattered radiation is intercepted, notably at a scatter angle of between 150° and 160°.

Figure 2:
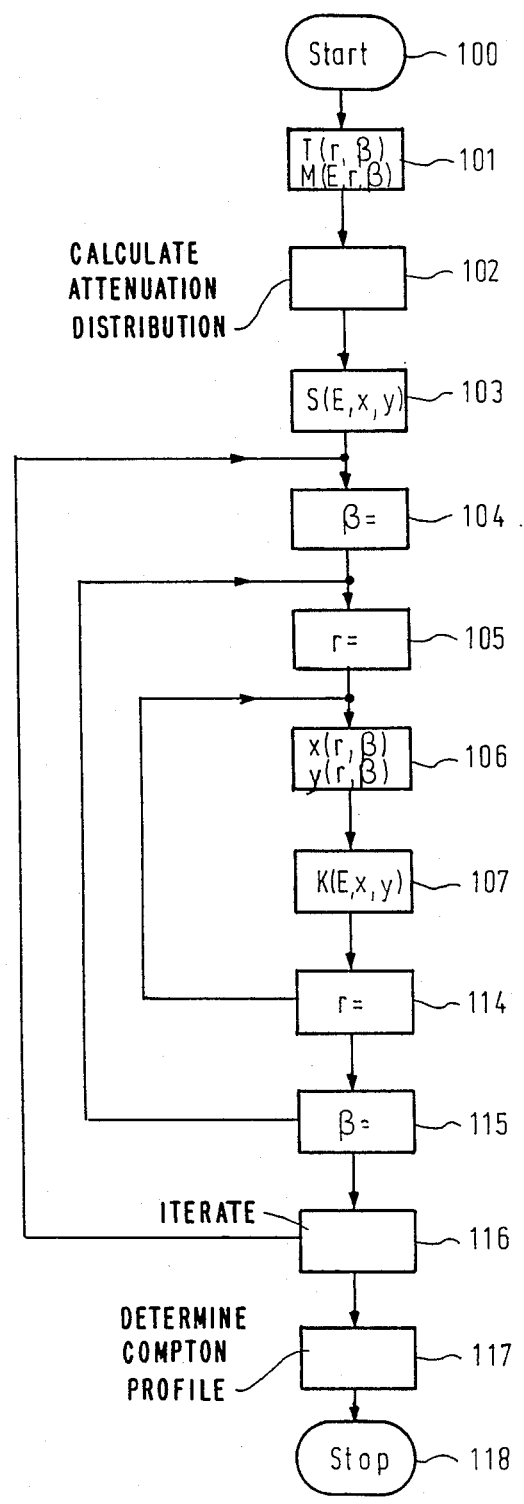
Figure 3:
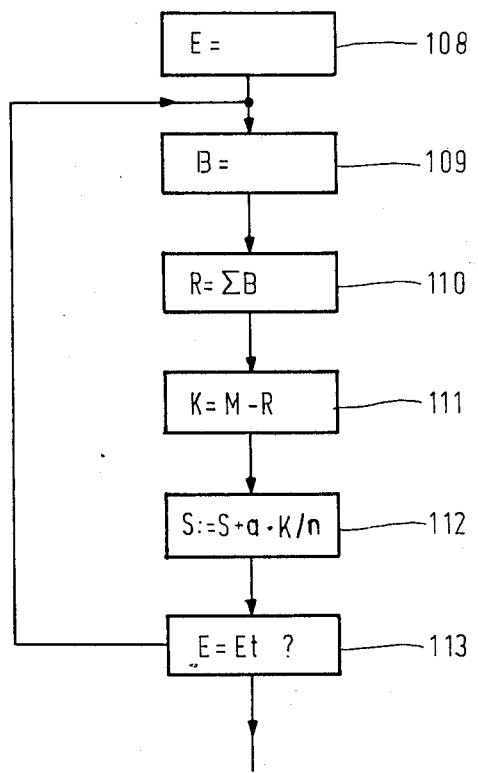

The invention will be described in detail hereinafter with reference to the drawing; therein:

FIG. 1 shows an apparatus for performing the method in accordance with the invention, FIG. 2 shows a flowchart for determining the Compton profiles for the various pixels, and FIG. 3 shows a flowchart of a sub-routine used in conjunction with FIG. 2.

The reference numeral 1 in FIG. 1 denotes a radiation source wherefrom a primary beam 2 having a small cross-section (pencil beam) is formed by means of a suitable primary beam diaphragm 3. The primary beam 2 passes through an examination zone 4 in which an object 5 to be examined, for example a human body, is positioned on a table. At the other side of the examination zone there is arranged a first detector 6 which measures the intensity of the primary beam 2 after its passage through the examination zone 4.

The radiation source 1, the primary beam diaphragm 3 and the detector 6 are mechanically coupled in a manner not shown. Using suitable drives, they can be displaced horizontally in the plane of drawing as well as rotated about the centre of the examination zone 4. As a result, the examination zone 4 can be scanned by the primary beam 2 along a multitude of parallel beam paths and from a multitude of different directions.

The output signal of the first detector 6 is applied, via an amplifier 7, to an analog-to-digital converter 8 so that the arithmetic device 9 coupled thereto receives a digital data work for each direction of each beam path. On the basis thereof, the arithmetic device can form a so-called transmission tomogram for determining the distribution of the attenuation, being determined essentially by Compton scattering, in the plane of the examination zone 4 scanned by the primary beam 2.

The device described thus far corresponds to the known first-generation computer tomography apparatus. However, the radiation source is a monochromatic radiation source which emits gamma quanta with an energy of a few 100 keV, for example the radio-isotope gold 198 which supplies gamma quanta with an energy of 412 keV.

In addition, the device comprises a second detector 10 which is mechanically rigidly coupled to the elements 1, 3 and 6. This detector, measuring the scattered radiation which is scattered at an angle of approximately 155° (i.e. backwards) has an energy-resolving power, i.e. it supplies pulses whose amplitude is proportional to the energy of the incident gamma quantum. The detector may be a semiconductor detector and may consist of, for example Ge or CdTe and the like.

The detector 10 is connected to the address inputs of a memory 13 via an amplifier 11 and an analog-to-digital converter 12. The operation of the analog-to-digital converter is fast enough and produces, in response to the detection of each X-ray quantum by the preceding detector 10, a signal which corresponds to the amplitude of the output signal of the detector. Each time when a voltage pule is converted into a digital data word in this manner, the address in the memory 12 corresponding to this data word is addressed. In synchronism with the analog-to-digital conversion, an adder 14 is activated which adds a one to the contents of the addressed memory location and which writes the result back into the same memory again. Thus, for each beam path of the primary beam through the examination zone the X-ray quanta are counted whose quantum energy has each time approximately the same value. The digital-to-analog converter 12, the memory 13 and the adder 14 thus act as a pulse amplitude analyzer which supplies a set of measurement values $M(E1)$, $M(E2)$, ... $M(et)$ which represent the intensity of the scattered radiation for different energy ranges E1, E2, ..., Et.

On the basis thereof and on the basis of the transmission computer tomogram calculated by means of the output signals of the detector 6, the arithmetic device 9 calculates for each pixel and for each energy or pulse transfer the scatter density in relation to the scatter angle (given by the position of the second detector 10 with respect to the examination zone 4). At the end of the calculation, for each pulse transfer an image of the scatter properties of the examination zone 4 will be stored in a memory device 15. The images can be displayed by means of a monitor 16. However, it is alternatively possible to reproduce for each pixel (or averaged over a plurality of pixels) the scatter properties as a function of the pulse transfer, i.e. the Compon profile.

The method of determining the Compton profiles will be described in detail hereinafter with reference to the flowchart given in FIG. 2. After the start (block 100), the measurement values of the detectors 6 and 10 are formed. The detector 6 supplies a set of measurement values $T(r,\beta)$ which are a measure for the transmission on the beam path in dependence of the distance r between this beam path and the centre of the examination zone 4 and which depend on the angle $\beta$ at which the beam path passes through the examination zone. The detector 10 supplies a set of measurement values $M(E,r,\beta)$ which also depend on r and $\beta$, but also on the energy E of the scattered radiation.

The attenuation distribution in the plane of the examination zone 4 irradiated by the primary beam is determined from the measurement values $T(r,\beta)$ (block 102). The reconstruction methods required for this operation are well known to those skilled in the art of computer tomography, so that they will not be elaborated herein.

During the next step of the program (block 103), the scatter coefficient $S(E,x,y)$ is given. The scatter coefficient represents the product of the scatter density and the differential scatter cross-section in relation to the space angle covered by the detector 10 as well as in relation to the relevant energy range (E1, E2, ... Et). The scatter coefficient of a pixel would be directly proportional to the measurement value for the relevant energy range which is supplied by the detector 10 and the pulse amplitude analyzer 12 to 14, if no scattering were to take place in the examination zone outside the pixel. The scatter coefficients $S(E,x,y)$ can be derived from the computer tomogram if the energy-dependency is assumed to be equal for all pixels and is multiplied by the attenuation value for the relevant pixel. However, it is alternatively possible to use the scatter coefficient $S(E,x,y)$ as a constant for each pixel and for each energy range. In that case he introduction should not take place during the reconstruction method; these values should rather be stored in a memory before the beginning of the execution of the method.

During the next two steps, the position of a beam path is given in that the angle $\beta$ is given at which the beam path extends through the examination zone (block 104) and in that the distance r between the beam path and the centre of the examination zone is given (block 105).

Subsequently, in a cartesian x-y coordinate system whose origin coincides with the centre of the examination zone and whose y axis is intersected by the beam path at the angle $\beta$, the coordinates $x(r,\beta)$ and $y(r,\beta)$ are determined for the pixels which are situated along the beam path in the examination zone (block 106). This determination is performed in accordance with the equation:

$$x \cos\beta + y \sin\beta = r \tag{1}$$

Subsequently (block 107), a correction value is formed for the pixels situated along the beam path defined by r and $\beta$ and for each of the energy ranges, said correction values being added to the stored value of the scatter coefficient for the same energy range and the same pixel. This correction value is chosen so that the deviation between the given value of the scatter coefficient and the actual value is reduced. This procedure will be explained hereinafter with reference to FIG. 3.

For a given energy range (E=E1—block 108), the contributin B by pixel to the signal generaged by the device 10 ... 14 is calculated. This contribution is calculated as follows:

$$B = c * S * Fp * Fs \tag{2}$$

Therein, S is the scatter coefficient, Fp is the attenuation experienced by the primary beam along the beam path to the relevant pixel (i.e. the fraction of the primary radiation which reaches the pixel), Fs is the attenuation experienced by the scattered radiation emerging from the pixel until it reaches the detector 10 (i.e. the fraction of the scattered radiation which is generated in the pixel and which reaches the detector 10), and c is a constant which is independent of the examination zone 4 and which depends only on the properties of the remainder of the apparatus (for example, the intensity of the radiation source 1, the sensitivity of the detector 10 etc.). The factor Fp can be derived directly from the previously calculated (block 102) computer tomogram, because the attenuation of the pixels situated along the beam path between the relevant pixel and the radiation source is known therefrom.

The factor Fs cannot be derived directly from the tomogram because the quantum energy of the scattered radiation is substantially lower than that of the primary radiation; for example, when the quantum energy in the primary beam amounts to 412 keV, for a scatter angle of 155° the maximum Compton scattering is obtained at an energy of approximately 162.4 keV. The attenuation of scattered radiation having an energy which is so much lower is substantially greater than that of the primary radiation. However, because the energy of the primary radiation is chosen so that the attenuation of the radiation takes place essentially by Compton scattering and because the ratio of the attenuations by Compton scattering for different energies is independent of the scatter properties of the body, the attenuation of the secondary radiation can be derived from the attenuation in the computer tomogram when the attenuation values in the pixels situated between the relevant pixel and the second detector 10 are multiplied by a constant factor. This factor corresponds to the total scatter cross-section for the energy of the scattered radiation, divided by the total scatter cross-section for the energy of the primary beam. The calculation of the total scatter cross-section for different energies is known from literature (for example, Hubbel "Photon Cross Sections, Attenuation Coefficients . . . ", published by the National Bureau of Standards, August 1969). For the energies of the scattered radiation this factor amounts to approximately 1.4.

Similarly, the contributions of all other pixels along the beam path followed by the primary beam are calculated and summed (block 110). The sume value R of these contributions should correspond to the measurement value M determined by the detector or the pulse amplitude analyzer for the same energy and for the same beam path if the given distribution of the scatter coefficients (block 103) were to correspond indeed with the distribution actually present in the examination zone. Because this is generally not the case, a correction value is formed (block 111) which corresponds to the difference between the measurement value M and the calculated value R, each time for the same beam path $r,\beta$ and for the same energy. The correction value K thus determined is divided by the number of pixels along the beam path and added, weighted by a factor a which is smaller than one, to the value S given for the relevant pixel xy and the relevant energy (block 112). The value thus formed already approximates the actual value better than the previously given value.

The steps 109 and 112 are repeated for the other energy ranges E2, E3, etc., until (block 113) the correction has also been performed for the last energy range $E = Et$.

Subsequently, a new beam path is determined by varying the value r, i.e. the distance between the beam path and the centre of the examination zone 4 (block 114), so that a beam path is given which adjoins the preceding beam path and which extends parallel thereto. For this beam path the steps 106 . . . 113 are repeated, after which the next beam path is given etc., until the correction has been performed for all beam paths extending through the examination zone at the angle $\beta$.

Subsequently, a different direction $\beta$ of the beam paths is given (step 115) and the steps 105 to 114 are repeated until all angular positions in which the primary beam has passed through the examination zone during the measurement have been processed.

This iteration operation may be followed (block 116) by further iterations where the steps 104 to 115 are repeated a number of times. The number of iterations may be fixed. However, it is alternatively possible to interrupt the iteration when the corrections (block 111) continuously drop below a given threshold value. In that case a corrected distribution S(E,x,y) is obtained which suitably approximates the actual distribution.

As is known, the following relationship exists be between the quantum energy E of the scattered radiation and the pulse transfer Q:

$$Q = 1/c^* \sqrt{E^2 p + E^2 - 2E\, E_p \cos a} \qquad (3)$$

where c is the velocity of light, Ep is the quantum energy of the primary beam, and a is the scatter angle. Consequently, the values S(E) iteratively determined for each pixel by means of the described method can be converted into values S(Q) which can also be standardized, if desired, so that the integral $\int S(Q)dQ$ equals the scatter coefficient of the transmission image for the relevant pixel, and which represent the variation of the Compton profile for the relevant pixel. The construction is then completed (block 118).

Because an unambiguous relationship between the pulse transfer and the energy of the scattered quanta for a given scatter angle, the measurement values determined in the step 101 for the individual beam paths as a function of the energy can also be given as a function of the pulse transfer. In that case the scatter coefficients for the individual pixels are given as a function of the pulse transfer in the block 103, after which the described conversion of the scattered radiation spectrum into a Compton profile in block 117 can be omitted.

What is claimed is:

1. A device for determining a two dimensional Compton profile image of an examination plane which is divided into pixels comprising:
    a radiation source which generates monochromatic radiation at an energy which is attenuated essentially by Compton scattering in the examination plane;
    a diaphragm which forms a primary pencil beam of said monochromatic radiation from the source which passes through the examination plane;
    means which redirect the primary beam so that it passes through the examination plane along a multitude of parallel beam paths in a multitude of directions;

first detector means disposed to measure the intensity of the primary beam which emerges from examination zone;

second, energy resolving detector means disposed to measure the intensity, as a function of energy, of scattered radiation which emerges from the examination zone at a selected angle with respect to the primary beam;

pulse amplitude analyzing means coupled to said second detector means; and arithmetic computing means coupled to the pulse amplitude analyzing means and the first detector means which iteratively determines the Compton profile of pixels corresponding to elemental areas in the examination zone from values measured by the first and second detector means by:

reconstructing attenuation values for the primary beam in the pixels from the measurements of the intensity of the emerging primary beams;

calculating, from the attenuation distribution and a known dependence of Compton scatter density upon quantum energy, the intensity of Compton scattered radiation for each beam path; and then calculating the difference between the measured intensity and the calculated intensity of Compton radiation for each beam path and determining correction factors for the Compton scatter density in the pixels therefrom.

2. A device as claimed in claim 1 wherein the radiation source comprises a radioactive isotope source.

3. The device of claim 2 wherein the radioactive isotope comprises gold 198.

4. A device as claimed in claim 1 wherein the selected angle is greater than 90°.

5. A method for two dimensional Compton profile imaging of an examination plane within an object, said examination zone being divided into pixels, comprising the steps of:

directing a monochromatic primary pencil beam of radiation which has an energy chosen so that attenuation of the primary beam in the examination plane is caused essentially by Compton scattering through the examination plane;

measuring the intensity of the primary beam which emerges after passing through the examination plane;

measuring the intensity, as a function of wavelength, of scattered radiation which emerges from the examination plane at a predetermined angle with respect to the primary beam;

redirecting the primary beam so that it passes through the examination plane along a multitude of parallel beam paths in a multitude of directions and repeating the measuring steps for each of said paths;

reconstructing attenuation values for the primary beam in the pixels from the measurements of the intensity of the emerging primary beams;

calculating, from the attenuation distribution and a known dependence of Compton scatter density upon quantum energy, the intensity of Compton scattered radiation for each beam path; and then calculating the difference between the measured intensity and the calculated intensity of Compton radiation for each beam path and determining correction factors for the Compton scatter density in the pixels therefrom.

6. A device for determining a two dimensional Compton profile image of an examination plane which is divided into pixels comprising:

a radiation source which generates monochromatic radiation at an energy which is attenuated essentially by Compton scattering in the examination plane;

a diaphragm which forms a primary pencil beam of said monochromatic radiation from the source which passes through the examination plane;

means which redirect the primary beam so that it passes through the examination plane along a multitude of parallel beam paths in a multitude of directions;

first detector means disposed to measure the intensity of the primary beam which emerges from examination zone;

second, energy resolving detector means disposed to measure the intensity, as a function of energy, of scattered radiation which emerges from the examination zone at a selected angle with respect to the primary beam;

pulse amplitude analyzing means coupled to said second detector means; and arithmetic computing means coupled to the pulse amplitude analyzing means and the first detector means which iteratively determines the Compton profile of pixels corresponding to elemental areas in the examination zone from values measured by the first and second detector means.

7. A device as claimed in claim 6 wherein the radiation source comprises a radioactive isotope source.

8. The device of claim 7 wherein the radioactive isotope comprises gold 198.

9. A device as claimed in claim 6 wherein the selected angle is greater than 90°.

* * * * *